US00PP22445P2

(12) United States Plant Patent
Giesen

(10) Patent No.: US PP22,445 P2
(45) Date of Patent: Jan. 3, 2012

(54) ***SOLENOSTEMON* PLANT NAMED 'MOS LAVRED'**

(50) Latin Name: *Solenostemon scutellarioides*
Varietal Denomination: Mos Lavred

(75) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/807,479

(22) Filed: Sep. 7, 2010

(51) Int. Cl.
*A01H 5/00* (2006.01)

(52) U.S. Cl. ..... Plt./373

(58) Field of Classification Search ..... Plt./373
See application file for complete search history.

*Primary Examiner* — Susan McCormick Ewoldt
(74) *Attorney, Agent, or Firm* — S. Matthew Edwards

(57) ABSTRACT

A new *Solenostemon* plant named 'Mos Lavred' particularly distinguished by the foliage color of narrow red centers with deep red-purple borders and light green margins with an upright but semi-compact and bushy habit that is well branched and uniform.

1 Drawing Sheet

Latin name of the genus and species of the plant claimed: *Solenostemon scutellarioides.*

Varietal denomination: 'Mos Lavred'.

BACKGROUND OF THE NEW PLANT

The present invention comprises a new *Solenostemon,* botanically known as *Solenostemon scutellarioides,* and hereinafter referred to by the variety name 'Mos Lavred'.

'Mos Lavred' is a product of a planned breeding program. The new cultivar has foliage color of narrow red centers with deep red-purple borders and light green margins, with an upright but semi-compact and bushy habit that is well branched and uniform.

'Mos Lavred' originated from a hybridization made in January 2006 in a controlled breeding environment in Andijk, Netherlands. The female parent was the unpatented, proprietary plant designated 'CS06-1-1' with lighter red-brown coloring with smaller leaves and longer and fewer stems.

The male parent of 'Mos Lavred' was an unpatented proprietary identified as 'CS06-4-1' with less red coloring, longer, thinner stems, and thinner leaves.

'Mos Lavred' was selected as one flowering plant within the progeny of the stated cross in September 2006 in a controlled environment in Andijk, Netherlands.

The first act of asexual reproduction of 'Mos Lavred' was accomplished when vegetative cuttings were propagated from the initial selection in September 2006 in a controlled environment in Andijk, Netherlands.

BRIEF SUMMARY OF INVENTION

Horticultural examination of plants grown from cuttings of the plant initiated in September 2006, and continuing thereafter, has demonstrated that the combination of characteristics as herein disclosed for 'Mos Lavred' are firmly fixed and are retained through successive generations of asexual reproduction.

'Mos Lavred' has not been observed under all possible environmental conditions. The phenotype may vary significantly with variations in environment such as temperature, light intensity and day length.

A Plant Breeder's Right for this cultivar was applied for in Canada on Feb. 18, 2010 (#10-6843). 'Mos Lavred' has not been made publicly available more than one year prior to the filing of this application.

The following traits have been repeatedly observed and are determined to be basic characteristics of the new variety. The combination of these characteristics distinguishes this *Solenostemon* as a new and distinct variety.

BRIEF DESCRIPTION OF THE PHOTOGRAPHS

The accompanying photographic drawing shows typical foliage characteristics of 'Mos Lavred' with colors being as true as possible with an illustration of this type. The photographic drawing shows a potted plant of the new variety.

DETAILED BOTANICAL DESCRIPTION

The plant descriptions, measurements and aforementioned photographs were taken in mid-June 2010 in Andijk, Netherlands. These plants were about 12 weeks old grown in a greenhouse in a bench trial in 4 inch pots.

Color references are made to The Royal Horticultural Society Colour Chart (R.H.S.) 2001.

TABLE 1

DIFFERENCES BETWEEN THE NEW VARIETY 'MOS LAVRED' AND A SIMILAR VARIETY

| | 'Mos Lavred' | 'Copper' (U.S. Plant Pat. No. 14,394) |
|---|---|---|
| Foliage color: | More red-brown | Less red-brown |
| Foliage shape: | Ovate | Deltoid |
| Stem length: | Shorter | Longer |
| Petiole color: | RHS 144C | RHS 183D |
| Petiole length: | Shorter | Longer |

Plant:

*Form, growth and habit.*—Annual potted or garden plant grown for its distinctive and colorful foliage; Stems strong, upright and freely branching-depending on the type and timing of terminal pinching; moderately vigorous growth habit.

*Plant height.*—34-38 cm.

*Plant width.*—33-39 cm.

*Garden performance and tolerance to weather.*—Very good.

Roots:

*Number of days to initiate roots.*—About 4 days at about 22 degrees C.

*Number of days to produce a rooted cutting.*—6-8 days at 22 degrees C.

*Type.*—Fine, fibrous, free branching.

*Color.*—RHS N155B but whiter.

Foliage:

*Arrangement.*—Opposite, simple.

*Immature, leaf color, upper surface.*—The center color closest to RHS 50A in a narrow pattern; the major portion of the leaf is closest to RHS 59A; and the margins are RHS 141C.

*Lower surface.*—RHS 50C in the center close to the veins, the major part of the leaf is RHS 52B and the margins of RHS141B.

*Mature, leaf color, upper surface.*—The center color closest to RHS 50A and RHS 50B in a narrow pattern; the major portion of the leaf is closest to RHS 59A to RHS 59B; and the margins are RHS 141C.

*Lower surface.*—RHS 50C in the center close to the veins, the major part of the leaf RHS 52B and the margins of the leafs are RHS 141B.

*Length.*—8.8-11.0 cm.

*Width.*—4.2-6.6 cm.

*Shape.*—Ovate.

*Base shape.*—Attenuate.

*Apex shape.*—Acuminate.

*Margin.*—Denate to serrate.

*Texture, upper surface.*—Pubescent, hirsute.

*Lower surface.*—Pubescent, hirsute mainly on the vein.

*Color of veins, upper surface.*—About RHS 59B.

*Color of veins, lower surface.*—About RHS 60B.

*Petiole color.*—RHS 144C.

*Length.*—2.3-2.5 cm.

*Diameter.*—0.4-0.6 cm.

*Texture.*—Pubescent, scattered pilose.

Stem:

*Quantity of main stems.*—6-10.

*Color of stem.*—RHS 60C.

*Length of stem.*—25-34 cm.

*Diameter.*—0.8 cm.

*Length of internodes.*—2.6-6.6 cm.

*Texture.*—Pubescent, pilose at axis.

Inflorescence: Flowering development was not observed on this plant to this date. Therefore also, seed development has not been observed.

Disease/pest resistance: Disease/pest resistance has not been observed.

What is claimed is:

1. A new and distinct variety of *Solenostemon* plant named 'Mos Lavred' substantially as illustrated and described herein.

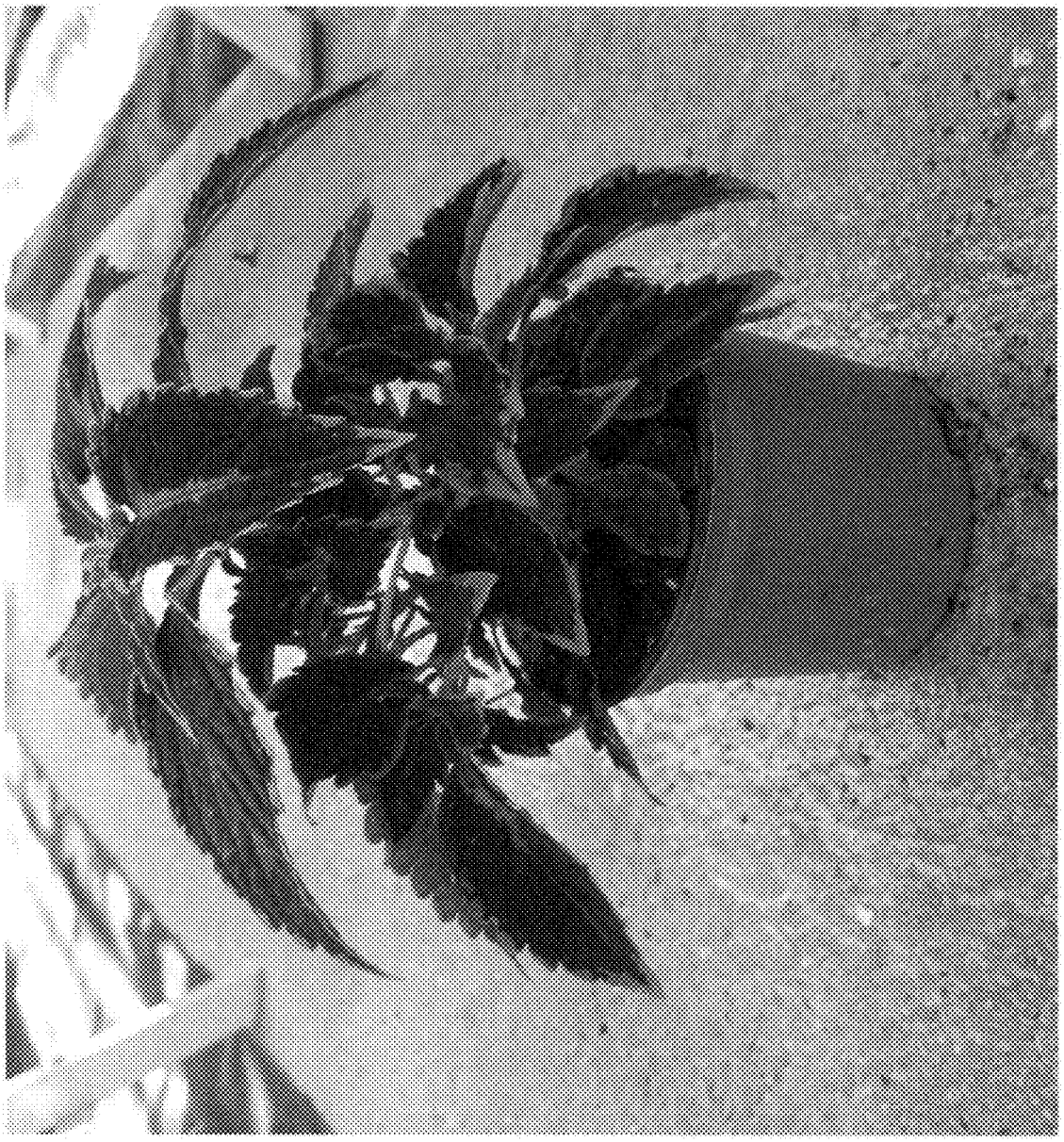

* * * * *